United States Patent [19]

Weingarten et al.

[11] Patent Number: 4,569,907
[45] Date of Patent: Feb. 11, 1986

[54] THIOPEPTOLIDE SUBSTRATES FOR VERTEBRATE COLLAGENASE

[75] Inventors: Harold I. Weingarten; Joseph Feder, both of University City, Mo.

[73] Assignee: Monsanto Company, St. Louis, Mo.

[21] Appl. No.: 571,227

[22] Filed: Jan. 16, 1984

[51] Int. Cl.$^4$ .............................................. C12Q 1/38
[52] U.S. Cl. ................................. 435/23; 260/112.5 R
[58] Field of Search ..................... 435/23; 260/112.5 R

[56] References Cited

U.S. PATENT DOCUMENTS

| | | | |
|---|---|---|---|
| 4,138,394 | 2/1979 | Sakakibara et al. | 260/112.5 R |
| 4,176,009 | 11/1979 | Sakakibara et al. | 435/24 |
| 4,425,428 | 1/1984 | Weingarten | 435/23 |
| 4,443,367 | 4/1984 | Weingarten | 260/112.5 R |
| 4,466,919 | 8/1984 | Weingarten | 260/112.5 R |
| 4,507,389 | 3/1985 | Weingarten | 435/23 |

OTHER PUBLICATIONS

Chem. Abs., 92: 71555v, (1980).
Nagai et al., *Biochim. Biophys. Acta* 455, 521–524, (1976).
Masui et al., *Biochem. Med.* 17, 215–221, (1977).
Gray et al., *Biochem. Biophys. Res. Comm.* 101(4), 1251–1258, (1981).
McRae et al., *Biochemistry* 20, 7196–7206, (1981).

*Primary Examiner*—Sidney Marantz
*Assistant Examiner*—Shawn P. Foley
*Attorney, Agent, or Firm*—Scott J. Meyer; James W. Williams, Jr.

[57] ABSTRACT

The disclosure relates to novel synthetic thiopeptolide substrates having high activity for the enzyme collagenase. These substrates have the following amino acid sequences:

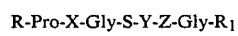

R-Pro-X-Gly-S-Y-Z-Gly-R$_1$ wherein
R = H or N-protecting group,
X = Leu, Ile, Phe, Val, Gln, Ala,
Y = Leu, Ile, Phe, Val, Ala,
Z = Leu, Ile, Phe, Val, Gln, Ala, and
R$_1$ = terminal amide, carboxyl or ester group.

6 Claims, No Drawings

THIOPEPTOLIDE SUBSTRATES FOR VERTEBRATE COLLAGENASE

BACKGROUND OF THE INVENTION

This invention relates to novel thiopeptolides which have high activity as substrates for vertebrate collagenase.

Collagenase is a proteolytic enzyme which acts on the protein collagen. This enzyme was early found in certain *clostridia* culture filtrates and shown to act specifically on native (undenatured) collagen at near physiological pH. See Mandl, "Collagenase and Elastases," *Advances in Enzymology* 23, p. 163, Interscience Publishers, New York, 1961. An illustrative example of a collagenase enzyme product obtained from special strains of *Clostridium histolyticum* is commercially available from Worthington Biochemical Corporation, Freehold, N.J.

Collagenolytic enzymes also have been obtained by tissue and cell culture from a wide range of animal species in which collagen is metabolized under both physiological and pathological conditions. Collagenase enzymes from such cell and tissue culture sources or from tissue extracts are usually obtained in exceedingly small amounts. Consequently, such enzymes are usually available only by laboratory preparation. An illustrative example of such a preparation is a purified collagenase obtained from culture media of tadpole explant as described by Nagai et al., *Biochim. Biophys. Acta* 263, 564–573 (1972).

The natural substrate collagen constitutes the connective tissue of the body and is the major type of fibrous protein in higher vertebrae, including mammals. In man, approximately one-third of the total protein content is collagen. The ability of collagenase to digest native collagen provides the enzyme with a variety of uses in tissue culture and cell studies including the isolation of tissue collagen and other types of tissue dissociation. Illustratively, achilles-tendon collagen is hydrolyzed by collagenase to peptides with an average chain length of four to five amino acids.

Collagenase also is believed to be associated with the tissue invasion process in tumor angiogenesis, in arthritic conditions such as rheumatoid arthritis, in corneal ulceration and other diseases of connective tissue. It has been suggested that tumor angiogenesis factor (TAF) induces collagenase secretion by blood vessel endothelial cells. See Moscatelli et al., *Cell* 20, 343 (1980). The ability of TAF to stimulate collagenase production in endothelial cells provides a basis for assay for TAF and anti-TAF. Accordingly, the measurement of collagenase production is a useful diagnostic tool for tissue invasion.

Conventional assays for collagenase generally are based on methodology developed by Mandl et al., *J. Clin. Invest.* 32, 1323 (1953). According to these assay procedures, collagenase is incubated for an extended period of time at 37° C. with native collagen. The extent of collagen breakdown is then determined using the Moore and Stein colorimetric ninhydrin method, *J. Biol. Chem.* 176, 367 (1948). Amino acids which are liberated are expressed as micromoles per milligram of collagenase. One unit of enzyme activity equals the amount of collagenase required to solubilize one micromole of leucine equivalents.

Various synthetic substrates also have been developed heretofore as reagents for the quantitative determination of proteolytic enzymes such as thrombin, plasmin, trypsin and collagenase. These substrates generally consist of relatively short chain peptides. Under the action of the appropriate enzyme, a fragment is hydrolytically split off from the substrate with the resulting formation of a split product, the quantity of which can be measured by conventional photometric, spectrophotometric, fluorescence-photometric, and chromatographic methods. The quantity of the split product formed per time unit is a measure for the enzyme activity from which the quantity of enzyme present in a given test sample can be calculated.

The following are examples of two such synthetic collagenase substrates which are commercially available from Peninsula Laboratories, San Carlos, Calif. and Cal-Med, South San Francisco, Calif.:

DNP-Pro-Leu-Gly-Ile-Ala-Gly-Arg-NH$_2$"

and

DNP-Pro-Gln-Gly-Ile-Ala-Gly-Gln-D-Arg-OH, wherein DNP=Dinitrophenyl.

In copending application Ser. Nos. 336,520, filed April 8, 1982, Ser. No. 450,318, filed Dec. 16, 1982 and Ser. No. 485,762, filed April 18, 1983, now U.S. Pat. Nos. 4,443,367; 4,466,919 and 4,425,428, respectively, assigned to a common assignee with this application, certain peptides and peptolides are disclosed which have substantially greater activity as collagenase substrates than the aforesaid commercially available substrates.

Other examples of peptide substrates for mammalian collagenase and methods of measuring collagenase activity with the substrates are described in U.S. Pat. Nos. 4,138,394 and 4,176,009; Nagai et al., *Biochim. Biophys. Acta* 445, 521–524 (1976); Masui et al., *Biochem. Med.* 17, 215–221 (1977); and Gray et al., *Biochem. Biophys. Res. Comm.* 101(4), 1251–1258 (1981). Further background information on mammalian collagenase also can be had by reference to the treatise "Collagenase in Normal and Pathological Connective Tissues," Woolley and Evanson, Eds., John Wiley & Son, New York, 1980.

DESCRIPTION OF THE INVENTION

In accordance with the present invention novel thiopeptolides have been synthesized as substrates for the enzyme collagenase. They have substantially greater activity than the aforesaid commercially available synthetic substrates for vertebrate collagenase and are useful in the spectrophotometric assay of the enzyme. The novel thiopeptolides of this invention are selected from the group consisting of:

R-Pro-X-Gly-S-Y-Z-Gly-R: (I)

wherein
R=H or N-protecting group,
X=Leu, Ile, Phe, Val, Gln, Ala,
Y=Leu, Ile, Phe, Val, Ala,
Z=Leu, Ile, Phe, Val, Gln, Ala,
R$_1$=terminal amide, carboxyl or ester group, and the pharmaceutically acceptable salts thereof.

The abbreviations used for the amino acids herein follow standard nomenclature in which:
Ala=L-alanine,
Gln=L-glutamine, Gly=glycine,
Ile=L-isoleucine,
Leu=L-leucine,
Phe=L-phenylalanine,
Pro=L-proline, and
Val=L-valine.

The N-protecting groups depicted as R in the structural formula I, above, are preferably alkanoyl, aroyl, or cycloalkanoyl and more preferably acetyl, benzoyl, carbobenzyloxy or t-butyloxycarbonyl.

The terminal groups depicted as $R_1$ in the structural formula I are preferably O-alkyl, O-aryl, NH-alkyl, NH-aryl, OH and $NH_2$ and more preferably $OC_2H_5$ or $NH_2$.

The term "aryl" as used herein refers to phenyl or phenyl substituted with one, two or three alkyl, alkoxy, halogen, amino, hydroxy or alkanoyloxy groups.

The terms "alkyl," alkanoyl, and "alkoxy," as used herein refer to groups having 1 to 8 carbon atoms.

The term "halogen" as used herein refers to fluorine, chlorine, bromine or iodine.

The pharmaceutically acceptable salts of the thiopeptolides of this invention include salts of cations, such as, for example, sodium, potassium, ammonium, calcium and magnesium as well as salts derived from either organic or inorganic acids such as, for example, acetic, lactic, tartaric, succinic, glutaric, benzoic, salicylic, methanesulfonic, toluenesulfonic, hydrochloric, sulfuric or phosphoric acids and the like. Desired salts can be prepared from other salts via conventional treatment with ion exchange resins. For non-pharmaceutical use such as in a spectrophotometric assay, the salt form need not be pharmaceutically or physiologically acceptable.

The initial peptide portion of the thiopeptolides of this invention can be made by appropriate adaptation of conventional methods for peptide synthesis. Thus, the peptide chain can be prepared by a series of coupling reactions in which the constituent amino acids are added to the growing peptide chain in the desired sequence. The use of various N-protecting groups, e.g., the carbobenzoxy group (CBZ) or the t-butyloxycarbonyl group (BOC), various coupling reagents, e.g., 1-ethyl-3-(3-dimethylaminopropyl)-carbodiimide hydrochloride (EDC), dicyclohexylcarbodiimide (DCC), carbonyldiimidazole, or 1-hydroxy-benzotriazole monohydrate (HBT), and various cleavage reagents, e.g., trifluoracetic acid, HCl in dioxane, boron tris(trifluoroacetate) and cyanogen bromide, and reaction in solution with isolation and purification of intermediates is well-known classical peptide methodology.

Preferably, the peptide is prepared by the well-known Merrifield solid support method. See Merrifield, *J. Amer. Chem. Soc.* 85, 2149–54 (1963) and *Science* 150, 178–85 (1965). This procedure, though using many of the same chemical reactions and blocking groups of classical peptide synthesis, provides a growing peptide chain anchored by its carboxyl terminus to a solid support, usually cross-linked polystyrene or styrene-divinylbenzene copolymer. This method conveniently simplifies the number of procedural manipulations since removal of the excess reagents at each step is effected simply by washing of the polymer.

The general reaction sequence for the Merrifield peptide synthesis can be illustrated as follows:

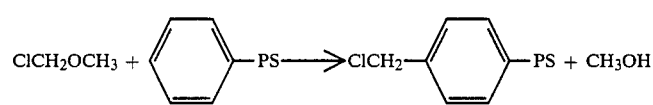

I.

Chloromethylation Step to provide reactive group for attachment of peptide, wherein PS = Polystyrene Residue.

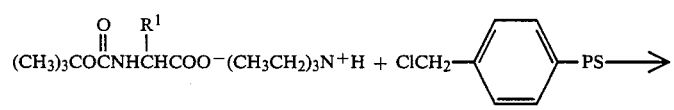

II.

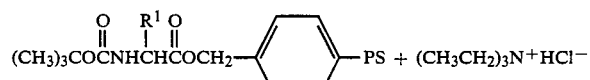

Esterification Step - Reaction with Triethylammonium salt of the First Protected Amino Acid ($R^1$) Using t-BOC Protecting Group.

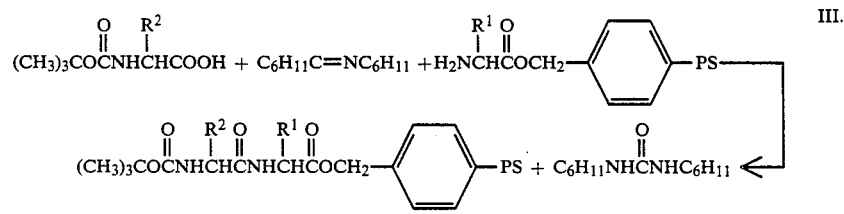

III.

Peptide forming step with Dicyclohexylcarbodiimide Coupling Agent.

This step follows cleavage of t-BOC by HCl and liberation of N-terminal amine by excess of triethylamine, thereby enabling it to react with the activated carboxyl of the next protected amino acid (R²). A final step involves cleavage of the completed peptide from the PS resin such as by anhydrous HBr in acetic acid or trifluoroacetic acid.

Further background information on the established solid phase synthesis procedure can be had by reference to the treatise by Stewart and Young, "Solid Phase Peptide Synthesis," W. H. Freeman & Co., San Francisco, 1969, and the review chapter by Merrifield in Advances in Enzymology 32, pp. 221–296, F. F. Nold, Ed., Interscience Publishers, New York, 1969. A suitable general method of the solid phase synthesis also is described in detail by Rivier et al, *Biopolymers* 17, 1927–1938 (1978).

The thiol-containing terminal portion of the novel thiopeptolides of this invention can be prepared by first converting an appropriate amino acid as defined by Y in the structural formula I, above, to its α-mercapto derivative and then coupling it to an appropriate amino acid Z-glycine ester as defined in structural formula I. The coupled product can then be further coupled to the initial peptide portion to form the full thiopeptolide.

For example, where amino acids Y and Z are both leucine in the structural formula I, the thiol-containing terminal portion of the thiopeptolide can be prepared by the following general synthetic scheme:

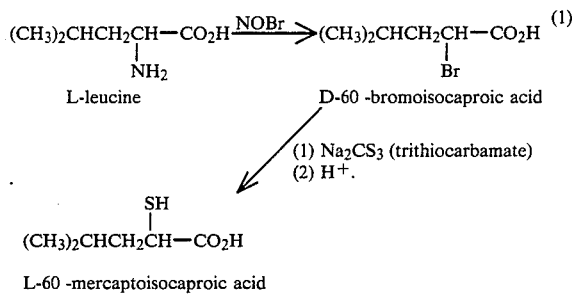

See, e.g., Yankeelov et al., *J. Org. Chem* 43, 1623–1624 (1978) for preparation of the L-α-mercaptoisocaproic acid by the foregoing reaction scheme.

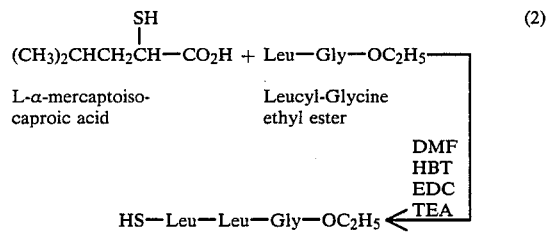

wherein
DMF = Dimethylformamide,
HBT = 1-Hydroxybenzotriazole,
EDC = 1-Ethyl-3-(3-dimethylaminopropyl)carbodiimide hydrochloride, and
TEA = Triethylamine.

Following preparation of the above thiol-containing terminal portion of the thiopeptolide, it can be further coupled to the initial peptide portion to form the full thiopeptolide. For example, where amino acid X is leucine in the structural formula I, the full thiopeptolide can be prepared by the following general reaction:

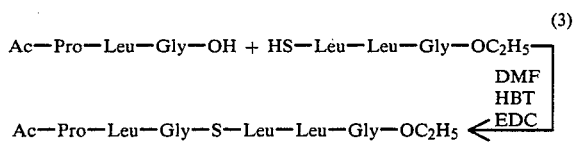

The leucine amino acids in the foregoing general reaction schemes can be replaced with equivalent amounts of other amino acids specified for X, Y and Z in the structural formula I, above, to provide analogous thiopeptolides in accordance with the present invention with substantially similar results. So also, N-protecting groups other than acetyl and terminal groups other than ethyl ester can be employed in the foregoing general reaction schemes with substantially similar results.

The preferred thiopeptolide Ac-Pro-Leu-Gly-S-Leu-Leu-Gly-OC₂H₅ is an excellent inhibitor (preinhibitor) of vertebrate collagenase by virtue of the fact that the enzyme cleaves this molecule to release HS-Leu-Leu-Gly-OC₂H₅. The compound HS-Leu-Leu-Gly-OC₂H₅ was found to have an $I_{50}$ (median inhibitory concentration) of $10^{-6}$M for vertebrate collagenase. The thiopeptolide is an inert molecule until it is brought into contact with vertebrate collagenase which effects the activation of the inhibitor and thereby deactivates the enzyme. Thus, the thiopeptolide when injected intravenously would be cleaved by circulating collagenase enzyme and the fragment would then act as an inhibitor of further activity of the enzyme.

Other examples of preferred thiopeptolides have the following structures:

Ac-Pro-Ala-Gly-S-Leu-Ala-Gly-OC₂H₅,

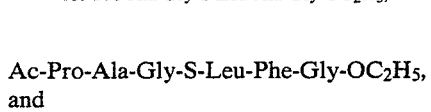
Ac-Pro-Ala-Gly-S-Leu-Phe-Gly-OC₂H₅,
and

Ac-Pro-Leu-Gly-S-Leu-Phe-Gly-OC₂H₅.

The high activity of the thiopeptolide as a substrate for vertebrate collagenase provides for its use in a rapid, sensitive, continuous spectrophotometric assay for the enzyme. Cleavage of the thiopeptolide by the enzyme at the thiol bond enables the determination continuously in the presence of 4,4'-dithiodipyridine or Ellman's reagent [DTNB, 5,5'-dithiobis(2-nitrobenzoic acid)].

The reaction of the released thiol from the thiopeptolide with 4,4'-dithiodipyridine or Ellman's reagent frees a chromophoric molecule which can be measured spectrophotometrically. For background information on Ellman's reagent for use in colormetric assay of enzymes, see Ellman, *Arch. Biochem. Biophys.* 82, 70–77 (1959), and Green and Shaw, *Anal. Biochem.* 93, 223–226 (1979); and for such use of 4,4'-dithiodipyridine, see McRae et al., *Biochemistry* 20, 7196–7206 (1981).

The following specific examples will further illustrate the invention although it should be understood that the invention is not limited to these specific examples.

EXAMPLE 1

Preparation of Ac-Pro-Leu-Gly-OH

This peptide is synthesized from the component amino acids by the solid phase method as follows:

A mixture of (5.5 g, 0.031 mole) N-t-BOC-glycine, (3.6 g, 0.062 mole) potassium fluoride and (20 g, 0.0028 mole) Merrifield resin (1% crosslinked polystyrene; 200–400 mesh, 1 m.eq. chloride/gram) is suspended in 100 ml dimethylformamide (DMF) and stirred at 50° for 24 hours. The resin is collected on a coarse fritted disk, washed twice with (DMF), 50% DMF in water, 50% ethanol in water and ethanol. The washed resin is then dried to a constant weight in vacuo yielding 25.4 g of N-t-BOC-glycine on resin which gives a negative ninhydrin test and an amino acid analysis showing 0.714 m.mole/g attachment. See Horicki et al., *Chem. Letters* 165–168 (1978) for background information on the general KF method of amino acid attachment to resin.

Other amino acids are added to the growing peptide chain by a series of coupling reactions using the desired N-t-BOC protected amino acids. The amino acids are selected such as to prepare the following peptide sequence:

Ac-Pro-Leu-Gly-OH wherein Ac=acetyl.

In each case, dicyclohexylcarbodiimide (DCC) is used as the coupling agent in methylene chloride solvent. After initial coupling, the α-amino protecting group is removed by trifluoracetic acid (TFA) in methylene chloride solvent followed by triethylamine (TEA) in methylene chloride. After removal of the α-amino protecting group, the remaining protected amino acids are coupled stepwise in the aforesaid order to obtain the desired peptide sequence. Each protected amino acid is reacted in excess DCC in methylene chloride solvent. After the amino acid sequence is completed, the peptide is removed from the resin support by treatment with anhydrous HF. At each step, excess reagents are removed by washing the resin with methanol and/or methylene chloride solvents.

The sequence of reaction and washing steps carried out for each amino acid addition to the growing peptide chain for preparation of the aforesaid peptides by the solid state peptide synthesis is set forth in the following Table I.

TABLE I

| Protocol Used for Solid-State Peptide Synthesis | |
|---|---|
| Wash or Reactant | Shake Duration |
| 1. Methylene chloride | 1 min. |
| 2. 50% TFA/methylene chloride | 1 min. |
| 3. 50% TFA/methylene chloride | 20 min. |
| 4. Methylene chloride | 1 min. |
| 5. Methylene chloride | 1 min. |
| 6. Methylene chloride | 1 min. |
| 7. 10% TEA/methylene chloride | 1 min. |
| 8. Methanol | 1 min. |
| 9. 10% TEA/methylene chloride | 1 min. |
| 10. Methylene chloride | 1 min. |
| 11. Methanol | 1 min. |
| 12. Methylene chloride | 1 min. |
| 13. Amino acid/methylene chloride | 1 min. |
| 14. DCC/methylene chloride | 30–90 min. |
| 15. Methylene chloride | 1 min. |
| 16. Methanol | 1 min. |
| 17. Methylene chloride | 1 min. |
| 18. Methanol | 1 min. |
| | 66–126 min. (1–2 hrs.) |

At step 14 the progress of the coupling is monitored by a ninhydrin color test.

The crude peptide, after removal from resin by hydrogen fluoride, is extracted into water, neutralized to pH 6–7 and the water is then removed in vacuo. A portion of the residue is redissolved in a minimum of water and pipetted onto a 2 cm×15 cm $C_{18}$ reverse-phase chromatographic column. The column is washed with three column volumes of water using a Gilson peristaltic pump. A step gradient of methanol/water, acetonitrile/water or acetonitrile/water-pH 2.5 (trifluoroacetic acid) is passed through the column to selectively elute components. The eluted fractions are monitored by HPLC and fractions rich in the desired component are pooled and lyophilized.

EXAMPLE 2

Preparation of Ac-Pro-Ala-Gly-OH

This peptide was prepared substantially similarly as Ac-Pro-Leu-Gly-OH, above, except that an equivalent amount of the N-t-BOC protected alanine instead of leucine was used in the amino acid coupling sequence.

EXAMPLE 3

Preparation of D-α-Bromoisocaproic Acid

To a solution of D-leucine (29 g, 0.22 mol) and KBr (90 g, 0.76 mol) in 450 ml 2.5 N $H_2SO_4$ cooled to 0° was slowly added, portionwise, $NaNO_2$ (23 g, 0.333 mol) over a period of one and one half hours. The reaction mixture was stirred at 0° for one hour after addition, then stirred five hours at room temperature. The organic phase was extracted into ethyl ether and the ether extract washed with water and dried over magnesium sulfate. The magnesium sulfate was removed by filtration and the filtrate concentrated in vacuo, yielding 37.5 g (87%) of crude bromide. The D-α-bromoisocaproic acid, a liquid, was twice distilled at reduced pressure through an 80 mm Vigieux column, yielding 18 g of product, bp 70°–73° 0.25 mm with a consistent nmr and mass spectrum $[a]_D^{20} = +42°$ (2, methanol).

EXAMPLE 4

Preparation of L-α-Mercaptoisocaproic Acid

To a solution of D-α-bromoisocaproic acid (17 g, 0.087 mol) in 40 ml water adjusted to pH 5–6 with NaOH and cooled in ice was added 70 ml of 2.2 M sodium trithiocarbonate. The resulting solution was allowed to stand at room temperature overnight. The aqueous solution was washed with ether, then acidified to pH 3 with $H_2SO_4$. The resulting organic phase was extracted into ether and dried over magnesium sulfate. The magnesium sulfate was removed by filtration and the filtrate concentrated in vacuo, yielding 13.2 g of crude mercapto compound, which was purified by fractional distillation through an 80 mm Vigieux column, bp 86°–87° (0.9 mm). The L-α-mercaptoisocaproic acid $[\alpha]_D^{20} -31°$, had a consistent nmr and mass spectrum.

EXAMPLE 5

Synthesis of L-Leucylglycine Ethyl Ester Hydrochloride

To a solution of leucylglycine (5 g, 27 mmol) in 30 ml ethanol cooled to 0° was added $SOCl_2$ (4.1 g, 35 mmol). The reaction solution was stirred overnight at room temperature. The ethanol was removed in vacuo, yielding a glassy product with a consistent mass spectrum, nmr and a single peak in the HPLC.

EXAMPLE 6

Synthesis of L-Penylalanylglycine Ethyl Ester Hydrochloride

This peptidyl ester hyrochloride was prepared substantially similarly as L-Leucylglycine ethyl ester hydrochloride, above, except that an equivalent amount of the dipeptide phenylalanylglycine was used instead of leucylglycine in the esterification reaction.

EXAMPLE 7

Synthesis of L-Alanylgylcine Ethyl Ester Hydrochloride

This peptidyl ester hydrochloride was prepared substantially similarly as L-Leucylglycine ethyl ester hydrochloride, above, except that an equivalent amount of the dipeptide alanylglycine was used instead of leucylglycine in the esterification reaction.

EXAMPLE 8

Preparation of HS-Leu-Leu-Gly-$OC_2H_5$

To a solution of L-α-mercaptoisocaproic acid (1 g, 6.8 mmol) and L-leucylglycine ethyl ester hydrochloride (2.0 g, 7.9 mmol) in 40 ml dimethylformamide was added HBT (1.1 g, 7.1 mmol) followed by addition of triethylamine (1.1 ml, 8.0 mmol) and EDC (1.6 g, 8.3 mmol). The solution was stirred at room temperature overnight. The triethylamine hydrochloride was removed by filtration and the filtrate concentrated in vacuo. The residue was partitioned between ethyl acetate and water and the organic layer was washed consecutively with dilute hydrochloric acid, water and sodium bicarbonate solution adjusted to pH 8.0. The ethyl acetate was dried over magnesium sulfate. The magnesium sulfate was removed by filtration and the filtrate concentrated in vacuo yielding 0.86 g of syrupy product. The crude HS-Leu-Leu-Gly-$OC_2H_5$ was used in the next step without further purification.

EXAMPLE 9

Preparation of HS-Leu-Phe-Gly-$OC_2H_5$

This mercaptopeptidyl ester was prepared substantially similarly as HS-Leu-Leu-Gly-$OC_2H_5$, above, except that an equivalent amount of L-phenylalanylglycine ethyl ester hydrochloride was used in the coupling reaction instead of L-leucylglycine ethyl ester hydrochloride.

EXAMPLE 10

Preparation of HS-Leu-Ala-Gly-$OC_2H_5$

This mercaptopeptidyl ester was prepared substantially similarly as HS-Leu-Leu-Gly-$OC_2H_5$, above, except that an equivalent amount of L-alanylglycine ethyl ester hydrochloride was used in the coupling reaction instead of L-leucylglycine ethyl ester hydrochloride.

EXAMPLE 11

Preparation of Ac-Pro-Leu-Gly-S-Leu-Leu-Gly-$OC_2H_5$

To a solution of Ac-Pro-Leu-Gly-OH (0.7 g, 2.1 mmol), HS-Leu-Leu-Gly-$OC_2H_5$ (0.6 g, 1.7 mmol) and HBT (0.26 g, 1.7 mmol) in 15 ml dimethylformamide was added EDC (0.4 g, 2.1 mmol). The solution was stirred at room temperature overnight. The solvent was removed in vacuo and the residue partitioned between salt water and ethyl acetate. The ethyl acetate layer was washed consecutively with dilute sodium bicarbonate in salt (NaCl) water, dilute hydrochloric acid in salt water, salt water, 1.0 mM cupric sulfate in salt water (to remove any mercapto products) and finally salt water. The ethyl acetate was dried over magnesium sulfate. The magnesium sulfate was removed by filtration and the filtrate concentrated in vacuo, yielding 0.8 g (73%) glassy residue of crude thiopeptolide product. A 100 mg sample of this crude product was purified by low pressure $C_{18}$ column chromatography. The purified thiopeptolide, had an acceptable amino acid analysis, a consistent mass spectrum and a single peak on HPLC analysis. Anal. Calcd. for $C_{31}H_{53}N_5O_8$ S.$3H_2O$: C, 52.4; H, 8.3; N. 9.9. Found: C, 52.5; H, 7.9; N. 9.9.

EXAMPLE 12

Preparation of Ac-Pro-Ala-Gly-S-Leu-Phe-Gly-$OC_2H_5$

This thiopeptiolide was prepared substantially similary as Ac-Pro-Leu-Gly-S-Leu-Phe-Gly-$OC_2H_5$, above, except that an equivalent amount of Ac-Pro-Ala-Gly-OH was used in the coupling reaction instead of Ac-Pro-Leu-Gly-OH.

EXAMPLE 13

Preparation of Ac-Pro-Ala-Gly-S-Leu-Ala-Gly-$OC_2H_5$

This thiopeptolide was prepared substantially similarly as Ac-Pro-Ala-Gly-S-Leu-Phe-Gly-$OC_2H_5$, above, except that an equivalent amount of HS-Leu-Ala-Gly-$OC_2H_5$ was used in the coupling reaction instead of HS-Leu-Phe-Gly-$OC_2H_5$.

EXAMPLE 14

Spectrophotometric Assay for Collagenase

Collagenase was prepared from culture media of normal human skin fibroblasts substantially according to the procedure of Stricklin et al., *Biochem.* 16 1607 (1977). The enzyme (23 μg/ml in 0.5 M tris buffer [tris(-hydroxymethyl) amino methane], 0.01 M $CaCl_2$, pH 7.5) was activated by incubating 10 μl samples with one μl of trypsin (10 mg/ml in 1 mM HCl) for twenty minutes at room temperature followed by addition of 20 μl of soybean trypsin inhibitor (5 mg/ml in 0.05 M tris buffer, 0.01 M $CaCl_2$, pH 7.5).

The activated enzyme was diluted 100 to 2000 fold for use with each of the following substrate thiopeptolides:

Ac-Pro-Leu-Gly-S-Leu-Leu-Gly-$OC_2H_5$,

Ac-Pro-Leu-Gly-S-Leu-Phe-Gly-$OC_2H_5$,

Ac-Pro-Ala-Gly-S-Leu-Phe-Gly-$OC_2H_5$, and

Ac-Pro-Ala-Gly-S-Leu-Ala-Gly-OC$_2$H$_5$.

The spectrophotometric assay was carried out at substrate concentrations of from 0.01 mM to 5 mM in 0.05 M HEPES buffer (N-2-hydroxyethylpiperizine-N'-2-ethanesulfonic acid) with 0.01 M CaCl$_2$ at a pH of 6.5–7.0 and containing 0.5 mM to 1.0 mM 4,4'-dithiodipyridine (or Ellman's Reagent). The total reaction volume was 250 μl including 10 to 100 μl of the diluted activated enzyme. The reaction solutions were placed in 10 mm pathlength, self-masking microcuvettes and the hydrolysis followed using a Gilford model 250 spectrophotometer at 324 λ(410 λ for Ellman's Reagent) and equipped with a Gilford model 6051 recorder. The initial rates were limited to the first 5% of reaction and were corrected for non-enzymatic hydrolysis, which never exceeded 25% of the total reaction at pH 6.5–7.0. The 4,4'dithiodipyridine (or Ellman's Reagent) at 0.5 mM was in large excess under the initial rate assay conditions and was not rate limiting.

The following Table I sets forth the relative rates of hydrolysis in the above spectrophotometric assay using ther above thiopeptolides as substrates in comparison to the rates of hydrolysis assayed by High Performance Liquid Chromatography (HPLC) of two commercially available substrates for collagenase and two other substrates described in copending application Ser. No. 450,318, cited hereinbefore. HPLC assay was used for the latter four compounds since they did not contain any chromophores.

TABLE I

| Comparison of Substrate | |
|---|---|
| Substrate | Relative Rate |
| Ac—Pro—Leu—Gly—S—Leu—Leu—Gly—OC$_2$H$_5$ | 8800 |
| Ac—Pro—Leu—Gly—S—Leu—Phe—Gly—OC$_2$H$_5$ | 5900 |
| Ac—Pro—Ala—Gly—S—Leu—Phe—Gly—OC$_2$H$_5$ | 2800 |
| Ac—Pro—Ala—Gly—S—Leu—Ala—Gly—OC$_2$H$_5$ | 950 |
| Ac—Pro—Leu—Gly—Leu—Leu—Gly—OC$_2$H$_5$* | 250 |
| Ac—Pro—Leu—Gly—Leu—Ala—Gly—OC$_2$H$_5$* | 110 |
| DNP—Pro—Leu—Gly—Ile—Ala—Gly—Arg—NH$_2$** | 25 |
| DNP—Pro—Gln—Gly—Ile—Ala—Gly—Gln—D-Arg—OH** | 5 |

*U.S. Ser. No. 450,318
**Peninsula Laboratories, Inc.

EXAMPLE 15

Enzyme Selectivity for Thiopeptolide

The ability of five proteolytic enzymes other than collagenase to cleave the synthetic substrate Ac-Pro-Leu-Gly-S-Leu-Leu-Gly-OC$_2$H$_5$ was tested by hydrolysis and following spectrophotometrically as in Example 14. The following Table II sets forth the relative selectivity of these enzymes in comparison to vertebrate collagenase.

TABLE II

| Enzyme Selectivity | |
|---|---|
| Enzyme | Relative Rate |
| Vertebrate Collagenase* | 260 |
| Elastase | 12 |
| Kallikrein | 4.3 |
| α-Chymotrypsin | 2.0 |
| Trypsin | 0.07 |
| Carboxypeptidase Y | 0.03 |

*Same as in Example 14

Various other examples will be apparent to the person skilled in the art after reading the present disclosure without departing from the spirit and scope of the invention and it is intended that all such further examples be included within the scope of the appended claims. For example, the terminal ethyl groups in the foregoing thiopeptolides can readily be converted to other ester groups such as methyl, propyl, benzyl, p-nitrobenzyl or t-butyl ester groups; and other N-protecting groups such as t-BOC and carbobenzoxy can readily be used in place of the acetyl groups or the N-protecting group can readily be removed without departing from the basic and novel properties of the invention.

What is claimed is:

1. A method for the determination of collagenase in a biological sample comprising reacting an aqueous solution of said sample with a thiopeptolide substrate selected from the group consisting of R-Pro-X-Gly-S-Y-Z-Gly-R$_1$ wherein
R=H or N-protecting group,
X=Leu, Ile, Phe, Val, Gln, Ala,
Y=Leu, Ile, Phe, Val, Ala,
Z=Leu, Ile, Phe, Val, Gln, Ala,
R$_1$=terminal amide, carboxyl or ester group, and salts thereof, said reaction being carried out in the presence of an excess of 4,4'-dithiodipyridine or Ellman's reagent, and then measuring the resulting released chromophoric molecule spectrophotometrically.

2. The method of claim 1 in which
X=Leu or Ala,
Y=Leu, and
Z=Leu, Ala or Phe.

3. The method of claim 2 in which the thiopeptolide has the structure

Ac-Pro-Leu-Gly-S-Leu-Leu-Gly-OC$_2$H$_5$.

4. The method of claim 2 in which the thiopeptolide has the structure

Ac-Pro-Leu-Gly-S-Leu-Phe-Gly-OC$_2$H$_5$.

5. The method of claim 2 in which the thiopeptolide has the structure

Ac-Pro-Ala-Gly-S-Leu-Phe-Gly-OC$_2$H$_5$.

6. The method of claim 2 in which the thiopeptolide has the structure

Ac-Pro-Ala-Gly-S-Leu-Ala-Gly-OC$_2$H$_5$.

* * * * *

UNITED STATES PATENT AND TRADEMARK OFFICE
CERTIFICATE OF CORRECTION

PATENT NO. : 4,569,907
DATED : February 11, 1986
INVENTOR(S) : Harold I. Weingarten and Joseph Feder It is certified that error appears in the above—identified patent and that said Letters Patent is hereby corrected as shown below:

In col. 2, line 56, the formula "R-Pro-X-Gly-S-Y-Z-Gly-R:" should read --R-Pro-X-Gly-S-Y-Z-Gly-$R_1$--.

In col. 5, line 35, "D-60" should read --D-$\alpha$--.

In col. 5, line 42, "L-60" should read --L-$\alpha$--.

In Claim 1, col. 12, line 27, the clause beginning with the language "and salts thereof..." should not be indented under $R_1$, but should begin at the left hand margin of col. 12 since the clause does not modify $R_1$.

Signed and Sealed this

Thirteenth Day of May 1986

[SEAL]

Attest:

DONALD J. QUIGG

Attesting Officer

Commissioner of Patents and Trademarks